United States Patent [19]

Allinikov

[11] 4,331,871
[45] May 25, 1982

[54] FLUORESCENT DETECTION OF FLAWS

[75] Inventor: Sidney Allinikov, Yellow Springs, Ohio

[73] Assignee: The United States of America as represented by the Secretary of the Air Force, Washington, D.C.

[21] Appl. No.: 141,522

[22] Filed: Apr. 17, 1980

Related U.S. Application Data

[62] Division of Ser. No. 76,631, Sep. 18, 1979, Pat. No. 4,273,671.

[51] Int. Cl.³ .............................................. C09K 3/00
[52] U.S. Cl. .................................................. 250/302
[58] Field of Search ..................... 250/302; 252/65.52, 252/65.54, 301.19

[56] References Cited

U.S. PATENT DOCUMENTS

| | | | |
|---|---|---|---|
| 2,499,466 | 3/1950 | Forest et al. | 250/302 |
| 2,516,857 | 8/1950 | Forest et al. | 250/302 |
| 3,404,093 | 10/1968 | Borrows | 252/62.52 |
| 3,485,758 | 12/1969 | Borucki et al. | 252/62.54 |

*Primary Examiner*—Bruce C. Anderson
*Attorney, Agent, or Firm*—Donald J. Singer

[57] ABSTRACT

In a method for detecting flaws in the surface of a workpiece, initially microcapsules containing a fluorescent dye are deposited on the surface. After removal of excess microcapsules from the surface in order to reduce background fluorescence, the surface is visually inspected under ultraviolet light. The method overcomes many of the disadvantages of conventional inspection procedures, e.g., by eliminating use of emulsifiers and by materially shortening processing time.

10 Claims, No Drawings

FLUORESCENT DETECTION OF FLAWS

RIGHTS OF THE GOVERNMENT

The invention described herein may be manufactured and used by or for the Government of the United States for all governmental purposes without the payment of any royalty.

CROSS-REFERENCE TO RELATED APPLICATION

This aplication is a divisional of application Ser. No. 76,631 filed on 18 Sept. 1979 and issued 16 June 1981 as U.S. Pat. No. 4,273,671.

FIELD OF THE INVENTION

This invention relates to a process for the non-destructive testing of objects and structures for the purpose of detecting any flaws or cracks in their surfaces. In one aspect, it relates to a microencapsulated fluorescent dye for use in the detection process.

BACKGROUND OF THE INVENTION

Fluorescent penetrant inspection is the most widely used method for the non-destructive inspection of bodies or parts. While various improvements in penetrant formulations have been made over the years, the penetrant inspection process has remained virtually unchanged. In carrying out the process, the part after cleaning is immersed in the penetrant for some period time, e.g., twenty minutes, the part is then cleaned to remove all penetrant except that contained in defects, developer is applied to widen the penetrant indication, and the part is inspected under ultraviolet light.

In some cases removal of excess penetrant is accomplished by water washing. Certain of the more sensitive penetrants must first be emulsified to render them water washable and then water washed. Upon completion of this step, the part is dried, developer is applied, and the inspection is carried out under ultraviolet light. The procedure of applying penetrant, washing, drying, and developing can take as long as an hour and longer.

The above-described conventional non-destructive inspection process has a number of disadvantages which over the years have been of great concern to users. For example, excessive washing can result in removal of penetrant from defects and the application of emulsifier must be carefully controlled. When parts containing penetrant are moved into the emulsifier tank, the emulsifier eventually becomes contaminated with penetrant. As a result the emulsifier must be disposed of and replaced with fresh emulsifier. Inspection must be accomplished within a specific period of time after the developer is applied. If this period is exceeded, the fluorescent indication is lost.

As furnished by a manufacturer, penetrant material usually consists of penetrant, emulsifier and developer. The materials provided by one company are generally not interchangeable with the materials of another company. For example, one company's emulsifier cannot be used with another company's penetrant. This situation results in a supply and logistics problem that has often proven to be troublesome.

It is a principal object of this invention to provide a method for the non-destructive testing of objects that overcomes the various problems associated with the conventional test method.

Another object of the invention is to provide microcapsules containing a fluorescent dye that can be used in a non-destructive inspection method.

Other objects and advantages of the invention will become apparent to those skilled in the art upon consideration of the accompanying disclosure.

SUMMARY OF THE INVENTION

Broadly speaking, the present invention resides in articles of manufacture in the form of tiny plastic spheres or microcapsules containing a fluorescent dye. The spheres are formed by microencapsulating a fluorescent dye in a plastic material in accordance with procedures described in the literature. Any suitable plastic or resinous material can be used to encapsulate the fluorescent dye. Examples of such material include an ureaformaldehyde polymer, a phenolic resin, polymethylmethacrylate, polyvinyl acetate, polyvinyl chloride, and the like. The spheres have thin plastic walls, e.g., about 0.5 to 1.0 micron thick, that are generally flexible or compressible.

The plastic spheres generally have a diameter ranging from about 1 to 150 microns. Microspheres having a diameter of about 1 to 20 microns have been found to give satisfactory results in most instances. The larger diameter microcapsules are required when inspecting an object which may have wide cracks that extend through the object. Liquid penetrants cannot be used for detection of such defects and the smaller microspheres would pass through the cracks. Thus, it is only by utilization of microspheres of a size that will lodge in the cracks is it possible to inspect for wide, open cracks.

Any suitable fluorescent dye usually employed in dye penetrant compositions can be microencapsulated in a plastic material. Examples of dyes that can be used include those marketed as Zyglo ZL-30, Fluorol 7GA, Calcofluor Yellow, Azsol Brilliant Yellow 6GF, Rhodamine B, Calcolfuor White RW, Blancophor White AW, Auramine, and Eosine G. The fluorescent dyes are generally supplied in solution in a solvent, and the dye solution as received is microencapsulated to form the microcapsules containing the fluorescent solution. However, it is within the scope of the invention to dissolve any fluorescent dye in any encapsulatable liquid and thereafter form the microcapsules.

In a preferred embodiment, the present invention is concerned with a method for detecting flaws in the surface of bodies and workpieces such as structural elements or engine parts. In accordance with the non-destructive inspection method, microcapsules containing a fluorescent dye are deposited on the surface to be inspected for flaws, excess microcapsules are removed from the surface to reduce background fluorescence, and the surface is viewed under ultraviolet light. Any colored traces in the surface provide an indication of the presence of cracks or flaws. It is within the scope of the invention to apply a developing agent to the surface after removal of excess microcapsules. In certain instances, particularly on shiny surfaces and where microcapsules may have ruptured, the developing agent enhances the fluorescent indication of flaws.

In essence, the present method can be considered to be a "dry" process. Thus, a "dry" fluorescent material is utilized rather than the family of liquid materials employed in the conventional method. Only a short time, e.g., a few minutes, is required to carry out the steps of the method; no time critical steps are involved.

Another important consideration of the present invention is the use of spherical fluorescent microcapsules as a tool rather than a material. The particular spherical shape of the microcapsule facilitates the removal of excess spherical microcapsules from the surface of the workpiece prior to testing the workpiece for flaws in its surface. Removal of this excess material is essential in order to reduce background fluorescence in those surface areas ajacent to any test area. The reduced background fluorescence improves accuracy in detection of the flaws. The spherical capsules can be removed from a test surface much more readily than the liquid penetrants presently required with prior art methods.

Another distinct advantage of this invention in the non-destructive inspection field is that the fluorescent spherical capsules can be applied as a dry, free-flowing material onto the surface of the workpiece. This eliminates the time required for a liquid penetrant to dwell on a workpiece surface which is generally a minimum of thirty minutes. Also, the dry spheres are less susceptable to processing errors after deposition compared to the liquids described in the prior art.

Several procedures can be followed for applying or depositing the microcapsules on the surfaces to be inspected. The material can be applied by physically rubbing it over the surfaces with a suitable applicator such as a cotton swab. In a preferred procedure, the microcapsules are sprayed onto the surfaces employing a suitable spray apparatus. A paint spray gun or an air eraser spray apparatus can be used in the spraying operation. An aerosol spray unit of the type available in hardware stores can also be employed.

For dry deposition of the material, it is important that the microcapsules be dry, non-porous and free flowing. In the process of microencapsulation, a small portion of the microcapsules may leak dye as a result of being cracked. A small quantity of free dye can cause clogging of the deposition apparatus and can also make removal of excess background fluorescence more difficult. To ensure that no leakers are present, the microcapsules should desireably be washed with water and dried prior to use in the present method.

It is within the scope of the invention to disperse the microcapsules in a carrier liquid and then spray the dispersion onto the surfaces to be inspected. A suitable liquid is one that does not attack the encapsulating polymer and preferably evaporates rapidly upon contact with the surfaces. Examples of carrier liquids that can be used include ketones, such as methyl ethyl ketone, and water.

Several procedures can be followed in reducing background fluorescence by removal of excess microencapsulated materials which are not lodged in defects and cracks. These include both dry and wet removal procedures. Removal of the microcapsules by dry procedures can be accomplished by brushing with cotton swabs or medium bristle brushes, by vacuuming, by concurrent brushing and vacuuming, by air pressure, and by concurrent brushing and air pressure. Excess microcapsules can also be removed by rinsing the surfaces with a detergent-water solution or the rinsing operation can be accompanied by gentle scrubbing with a brush.

After removal of excess microcapsules, the surfaces are visually examined under an ultraviolet lamp for indications of porosity or cracks. Surfaces that have been subjected to a dry removal of microcapsules can be inspected without further processing. When a wet rinse is used, the surfaces are dried, e.g., by blotting with a lint-free paper towel, prior to inspection.

A more complete understanding of the invention can be obtained by referring to the following illustrative examples which are not intended, however, to be unduly limitative of the invention.

EXAMPLE I

A run was conducted in which dry microcapsules containing a Rhodamine B dye solution were sprayed on an engine turbine blade containing a large crack. The capsules ranged from 8 to 16 microns in diameter. A laboratory type paint spray gun (Model EGA-De Vilbiss Company) was used to apply the material to the blade surface. Excess microcapsules were removed from the turbine blade with a dry cotton swab. The capsules were easily removed from the blade surface except at the crack location in which capsules were lodged. The blade was examined under ultraviolet irradiation. The fluorescent indication was highly visible, giving a sharp, high resolution trace of the crack in the turbine blade.

EXAMPLE II

A series of runs was conducted in which the method of this invention was conducted in conjunction with two types of crack standards. The first type was a set of three chrome plated brass crack standards. Dimensions of the panels were 10 cm $\times$ 6.7 cm. Each of the three panels represented a specific maximum crack width. Crack widths were 12.7, 3.5, and 0.5 microns, respectively, for the coarse, medium, and fine crack standard panels. The second type of standards was made of steel bars with dimensions of 15.6 cm $\times$ 2.5 cm. The crack width of each of the two steel standards were 0.5 and 2.5 microns, respectfully. Prior to use in the present method, the crack standards were thoroughly cleaned.

Three different dye solutions and one commercially available fluorescent dye penetrant solution were microencapsulated according to well known procedures. The dyes encapsulated were Rhodamine B, Fluorol Yellow, and a substituted naphthalamide compound. The encapsulated penetrant solution was Zyglo ZL-L30. Diameters of the capsules containing the dye solutions ranged from 1 to 10 microns for the naphthalamide dye, 3 to 11 microns for the Fluorol Yellow, and 8 to 16 microns for the Rhodamine B. The capsule wall was an urea-formaldehyde polymer. The diameter of the capsules containing Zyglo ZL-30 dye penetrant ranged from 2 to 5 microns, and the capsule wall was a phenolic resin.

The microcapsules were deposited on the test surfaces by the following techniques:

(1) physically rubbing the capsules over the surfaces with a cotton swab;

(2) spraying the capsules through a laboratory size paint spray gun;

(3) spraying the capsules through an air eraser apparatus; and (4) applying the capsules with a PRE-VAL aerosol unit.

The paint spray gun (Model EGA—De Vilbiss Co.) was equipped with an F size needle and fluid tip and #390 air cap. A 4 oz. glass cup contained the capsules to be sprayed, and air pressures ranging from 25 to 80 psi were used.

The air eraser spray apparatus was made by the Paasche Airbrush Co. Nitrogen pressures ranging from 10 to 40 psi were used for application of the capsules.

The assembly of the aerosol spray unit consisted of a 6 oz. capacity glass container and a replaceable power pack containing a propellant, siphon tube, and spray nozzle.

The microencapsulated materials were applied dry in all runs with the exception of one run with the aerosol spray. In this run, the microcapsules were dispersed in methyl ethyl ketone and sprayed onto the first type of fine crack standard.

Both dry and wet removal procedures were followed in removing excess capsules not lodged in the defects and cracks. Removal of capsules by dry procedures were accomplished with cotton swabs, medium bristle brushes, concurrent brushing and vacuum, air pressure, and vacuum alone. In wet procedures, a rinse with a detergent-water solution alone and in conjunction with gentle rubbing with a medium hard bristle brush was used.

The test specimens were visually examined under an ultraviolet lamp for indications of porosity or cracks. Crack standards that had been subjected to a dry removal of excess capsules were inspected without further processing. Crack standards that had been wet cleaned were dried with a lint-free paper towel prior to inspection. The specimens were inspected both before and after application of a commercial developer to determine the effect and relative value of a developer in enhancement of crack indication.

Deposition problems were encountered with the urea-formaldehyde microencapsulated dye solutions when applied as dry powders from the different pieces of spray apparatus. The principal difficulty was intermittent clogging of the equipment which occurred regardless of the application spray pressure. The clogging was attributed to the presence of some free dye solution on the surfaces of the capsules and demonstrates the importance of using in spray applications dry, non-porous, and free flowing capsules. However, the capsules could be physically rubbed into cracks and thereby provide good indications. This deposition procedure would be useful for parts with flat, uncomplicated surfaces.

The microencapsulated Zyglo ZL-30 material with capsule diameters under 5 microns and in the form of a dry, free flowing powder was readily applied by all of the deposition procedures. Penetration of the cracks and indications were achieved on the first type of crack standards. Changes in the brightness of indications were noticeable between pressure changes up to 60 psi at the spray gun nozzle. Application pressures above 60 psi did not enhance brightness.

In the run in which microcapsules were dispersed in methyl ethyl ketone and sprayed on a fine crack standard of the first type, the panel was uniformly covered with capsules. The liquid carrier flashed off rapidly so that the workpiece surface was dry almost immediately after the spray application. The cracks could be readily observed upon subsequent inspection.

In general, removal of excess capsules was dependent upon the surface condition of the inspection specimens. Relatively smooth surfaces did not present a problem in dry or wet removal of excess capsules. The fluorescent background was very low and cracks in the standards could be readily discerned. Rough surfaces, especially in pitted areas, did present a capsule removal problem with the dry removal techniques. The most efficient dry capsule removal procedure appeared to be a combination of mechanical brushing concurrent with a vacuum cleaning action.

The best results in removing background fluorescent capsules were obtained by a rinse with a detergent-water solution prior to inspection. This procedure worked very well on both smooth and rough surfaces. The wet capsule removal technique was rapid and was not sensitive as to the time of removal after the capsules had been deposited on the specimen surfaces.

The test results indicated that capsule size is not necessarily indicative of the crack widths that can be entered. With capsules smaller than the cracks upon which they impinge, entry into the cracks occurs. Also, it was found that capsules (8-16 microns) larger than the cracks widths provided indications on the coarse, medium and fine crack standards. The mechanism by which this occurs is not entirely understood. However, the capsule walls are flexible and the capsules could under pressure wedge in a crack. Also, the capsules could break on rough crack edges, allowing penetrant to flow into cracks.

Best results were obtained when using microcapsules having a 2 to 5 micron diameter. These capsules contained Zyglo ZL-30, a Group VI penetrant meeting Spec. MIL-I-25135. The crack indications could be readily discerned under an ultraviolet lamp in all three crack standards of the first type. The corresponding electrographic print for the fine crack standard indicated the sensitivity of the microcapsules. The fluorescent indications were clearly identical to the lines in the electrographic print.

Treatment with Met-L-Check D-70 spray developer in some cases enhanced the brightness of the indications. Thus, on shiny surfaces the developer powder may reduce visible light reflection of the background surface, thereby improving contrast. Also, in some instances where capsules may break upon impact or shape edges of a crack, the developer may wick free liquid in the same manner as it works with conventional liquid penetrant formulations.

Inspection of the standards one week after deposition of the microcapsules revealed that the indications were still visible. No additional processing was required from that done the previous week.

As seen from the foregoing, the present invention provides a method for the non-destructive inspection of bodies that overcomes the several problems associated with the conventional inspection method. The microcapsules containing a fluorescent dye can be applied to the workpiece as a free flowing powder or in a dispersed form in water or other liquid carrier. As contrasted to conventional liquid penetrants, the microcapsules are insensitive to processing variations in application and removal prior to inspection. The processing time prior to inspection is much shorter than with conventional post emulsifier systems. For example, in the runs described above, the time period from spraying the mocrocapsules to inspection was a minute or two. The microcapsules can contain fluorescent compounds that otherwise could not be used because of toxicity problems.

As will be evident to those skilled in the art, modifications of the present invention can be made in view of the foregoing disclosure without departing from the spirit and scope of the invention.

I claim:

1. A method for the non-destructive testing of an object to detect flaws therein which comprises depositing on a surface of the object, spherical, compressible microcapsules containing a fluorescent dye; removing excess microcapsules from the surface; and viewing the surface under ultraviolet light.

2. The method according to claim 1 in which the microspheres have a diameter ranging from about 1 to 150 microns.

3. The method according to claim 2 in which excess microspheres are removed by concurrent brushing and vacuuming the surface.

4. The method according to claim 2 in which the microcapsules are removed by washing the surface with a water-detergent solution.

5. A method for the non-destructive testing of an object to detect flaws therein which comprises spraying on a surface of the object dry, free flowing, spherical, compressible microcapsules containing a fluorescent dye; washing the surface with a water-detergent solution so as to remove from the surface excess microspheres which are not lodged in a flaw; drying the surface; and viewing the surface under ultraviolet light.

6. The method according to claim 5 in which the microspheres have a diameter ranging from about 1 to 150 microns.

7. The method according to claim 5 in which developing agent is applied to the surface after washing and drying the surface.

8. A method for the non-destructive testing of an object to detect flaws therein which comprises dispersing in a liquid carrier plastic, spherical compressible microcapsules containing a fluorescent dye; spraying the resulting dispersion on a surface of the object, thereby covering the surface with microcapsules; allowing liquid carrier to evaporate from the surface; removing from the surface excess microcapsules which are not lodged in a flaw; and viewing the surface under ultraviolet light.

9. The method according to claim 8 in which the microcapsules are dispersed in methyl ethyl ketone.

10. The method according to claim 8 in which the microcapsules are dispersed in water.

* * * * *